(12) United States Patent
Rolf et al.

(10) Patent No.: US 10,512,526 B2
(45) Date of Patent: Dec. 24, 2019

(54) DENTAL COLORING STAMP AND A METHOD OF COLORING

(71) Applicant: 3M INNOVATIVE PROPERTIES COMPANY, St. Paul, MN (US)

(72) Inventors: Jacqueline C. Rolf, River Falls, WI (US); Andreas Herrmann, München (DE); Michael Jahns, Gilching (DE); Dajana Zimmermann, Ammersee (DE); Gallus Schechner, Herrsching (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 151 days.

(21) Appl. No.: 15/533,834

(22) PCT Filed: Dec. 3, 2015

(86) PCT No.: PCT/US2015/063584
§ 371 (c)(1),
(2) Date: Jun. 7, 2017

(87) PCT Pub. No.: WO2016/094154
PCT Pub. Date: Jun. 16, 2016

(65) Prior Publication Data
US 2017/0319305 A1 Nov. 9, 2017

(30) Foreign Application Priority Data
Dec. 11, 2014 (EP) .................................. 14197482

(51) Int. Cl.
*A61C 13/08* (2006.01)
*A61C 5/70* (2017.01)
*A61C 5/77* (2017.01)

(52) U.S. Cl.
CPC .............. *A61C 13/082* (2013.01); *A61C 5/70* (2017.02); *A61C 5/77* (2017.02)

(58) Field of Classification Search
None
See application file for complete search history.

(56) References Cited

U.S. PATENT DOCUMENTS 6,056,467 A 5/2000 De Laforcade
7,815,387 B2 10/2010 Gueret
(Continued)

FOREIGN PATENT DOCUMENTS

DE 2812146 9/1979
WO WO 2013-022612 2/2013
(Continued)

OTHER PUBLICATIONS

International Search Report for PCT International Application No. PCT/US2015/063584, dated May 24, 2016, 6 pages.

*Primary Examiner* — Shamim Ahmed
*Assistant Examiner* — Bradford M Gates
(74) *Attorney, Agent, or Firm* — 3M Innovative Properties Company (57) ABSTRACT

A dental coloring stamp has a transfer pad for transferring a dental coloring solution to a precursor of a dental restoration. The transfer pad is at least partially formed of an open-celled elastic sponge and has a free transfer surface. The cross-section of the transfer pad is greater than a circular area of 10 mm in diameter so that a side of a dental restoration precursor can be stamped and thus colored. The invention helps facilitating the coloring of dental restorations.

5 Claims, 5 Drawing Sheets

(56) References Cited

U.S. PATENT DOCUMENTS

2008/0311543 A1    12/2008  Viscomi
2012/0139141 A1*  6/2012  Khan .................. A61C 13/082
                                                          264/20
2013/0221554 A1*  8/2013  Jung ...................... B32B 18/00
                                                          264/16
2014/0178834 A1    6/2014  Jahns

FOREIGN PATENT DOCUMENTS

WO    WO 2013-029791      3/2013
WO    WO-2013170705 A1 *  11/2013  ............. C04B 41/85

\* cited by examiner

DENTAL COLORING STAMP AND A METHOD OF COLORING

FIELD OF THE INVENTION

The invention relates to a dental coloring stamp which is configured to color a dental restoration precursor by stamping a side of the dental restoration. The invention further relates to a method of coloring a dental restoration by stamping a side of the dental restoration.

BACKGROUND ART

In dentistry, the restoration of a patient's tooth or teeth generally includes the replacement of the natural tooth substance by an artificial substance. For larger restorations, pre-finished dental restorations or prostheses are commonly used to replace at least a part of the tooth or teeth.

In recent years ceramic and glass-ceramic materials have been widely used for making such dental restorations, because of their good physical, aesthetic and biocompatible properties. These restorations are often manufactured by an automated process, which typically includes:
 capturing the shape of a patient's teeth, for example by scanning;
 designing the shape of the dental restoration using computer-aided design (CAD) software; and
 manufacturing the dental restoration by an automated Computer Numerical Controlled (CNC) machine.

One common method of making dental restorations is based on providing a standardized blank of ceramic, glass-ceramic or glass material and machining the dental restoration from that blank by material removal. Some methods are further based on the use of blanks made of a pre-sintered material. Such pre-sintered material is typically provided by compacting ceramic/glass-ceramic particles to a blank which is subsequently fired or pre-sintered so that the particles cohere sufficiently to provide the blank with a certain mechanical stability and so that the blank still has an open-celled structure due to voids still present between adjacent particles. A so formed blank has a lower mechanical strength than the ceramic/glass-ceramic material from which it is made, and accordingly, such a blank can be machined relatively easily. The dental restoration can be obtained from such a blank by machining an oversized precursor of the dental restoration from that blank. This dental restoration precursor is typically fired or sintered until substantially all voids are eliminated to form the dental restoration. Due to the elimination of the voids the material shrinks during sintering so that the originally oversized dental restoration precursor converts into the appropriately sized dental restoration.

One technical challenge is the coloring of dental restorations to the desired tooth color. While there are advantages of using standardized blanks during manufacturing, it is generally desirable to provide a dental restoration at a color or color structure which resembles the color structure of a natural tooth. There have been attempts to color pre-sintered precursors of dental restorations with so-called dental coloring solutions.

Commercially available dental coloring solutions typically comprise water, metal cations selected from rare earth elements, transition metal and mixtures thereof, optionally complexing agent(s) and/or further additives like (poly) ethylene glycol. The coloring solutions are typically used for homogeneously coloring of porous dental ceramics. The coloring solutions are applied to the dental ceramic being in a porous and absorbent stage. After sintering, the dental ceramic usually shows a tooth-like color and can be directly used as a monolithic restoration or is ready for applying an additional veneering layer.

A dental restoration precursor can for example be immersed in such a dental coloring solution before it is sintered and thus may be provided with a desired tooth color. Further there have been attempts to provide different portions of the dental restoration with different colors, for example by applying different coloring solutions to different areas of the dental restoration precursor using a brush.

WO 2013/029791 A1 discloses a brush for applying a coloring solution to ceramics in the dental area. The brush comprises a brush tip, a connecting piece and a gripping piece. The gripping piece comprises a reservoir for receiving a color liquid and the connecting piece comprises a liquid depot.

While existing methods and tools for making dental restorations in desired individual colors provide certain advantages there is still a need for a method and device which are easy to use, relatively inexpensive and which allow the making of high quality dental restorations.

SUMMARY OF THE INVENTION

The invention relates in one aspect to a dental coloring stamp. The dental coloring stamp comprises a transfer pad for transferring a dental coloring solution to a precursor of a dental restoration. The transfer pad being at least partially formed of an open-celled elastic sponge. Further, the transfer pad has a thickness along a stamping dimension and a, preferably obtuse, transfer surface which extends in dimensions essentially laterally to the stamping dimension. The transfer pad in dimensions laterally to the stamping dimension is preferably greater than a circular area of 10 mm in diameter. Further the transfer pad in dimensions laterally to the stamping dimension is preferably greater than the greatest cross-section of a human molar tooth in a plane essentially parallel to the occlusal plane of the tooth.

The invention is advantageous in that it allows coloring of a dental restoration by a relatively simple method. A user of a dental coloring stamp of the invention may not need special training or a lot of experience as for example required for some methods of the prior art. Further the invention allows for providing a dental restoration with a color gradation with a single coloring solution only. Therefore the invention helps eliminating the need for applying several colors to obtain a color gradation. Furthermore, the invention provides a relatively inexpensive and easy to use dental coloring stamp suitable for performing the method of the invention. In particular the invention helps improving the reproducibility of the coloring process significantly and helps minimizing the variability naturally occurring during conventional coloring by individual operators. Further the invention minimizes the number of required manual steps that are prone to variations.

A dental restoration precursor as referred to in this specification is preferably made of a pre-sintered ceramic or glass-ceramic material. Such a dental restoration precursor can be sintered to form the dental restoration. Accordingly the dental restoration precursor and the dental restoration differ in their material structure. In particular the dental restoration precursor is preferably formed of a pre-sintered material and the dental restoration is preferably formed of a sintered material.

The sintered material referred to in this specification preferably has a material density in a range of 2 $g/cm^3$ to 3.5 g/cm³ (glass ceramic and glass materials) or 5.7 g/cm³ to 6.2 g/cm³ (zirconia ceramic materials), and the pre-sintered material preferably has a material density in a range of 30% to 92% of the material density of the sintered material. Preferably the material density of the pre-sintered material is in a range of 40% to 60% of the material density of the sintered material, and more preferably in a range of 45% to 55%. The pre-sintered material is further preferably open-celled.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. Materials with an open-celled structure are permeable to gases.

Typical values for an "open-celled" material are between about 15% and about 75% or between about 18% and about 75%, or between about 30% and about 70%, or between about 34% and about 67%, or between about 40% to about 68%, or between about 42% and about 67%.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. Sintering typically includes the densification of a porous material to a less porous material (or a material having less cells) having a higher density, in some cases sintering may also include changes of the material phase composition (for example, a partial conversion of an amorphous phase toward a crystalline phase).

Figure 6:
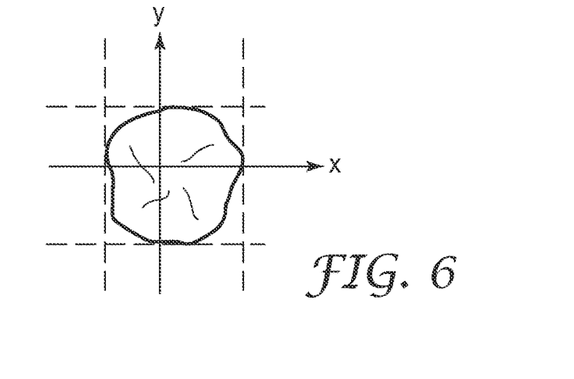
FIG. 6 illustrates in a top view an occlusal side of a dental restoration/dental restoration precursor.

For the purpose of the present specification a dental restoration and a dental restoration precursor each are assigned 6 sides. Each side is assigned one direction in a three-dimensional Cartesian coordinate system. A side for the purpose of the present specification corresponds to surface areas of the dental restoration/dental restoration precursor which are visible in a plan view from one direction along a dimension of the three-dimensional Cartesian coordinate system. As an example FIG. 6 illustrates the occlusal side of a dental restoration precursor in a top view along a Z dimension (perpendicular to the plane of the Figure). The boundary of the occlusal side is formed by the outline of the dental restoration precursor in that plan view.

In one embodiment the stamping surface has a convex dome-shape being defined by an outer cross-section with a minimum width in a plane laterally to the stamping dimension, a height along the stamping dimension between said plane and the dome apex, and a ratio between the height and the minimum width of less than 1:1, respectively. For example the transfer pad may have a generally cylindrical section and a further section forming the stamping surface. The stamping surface may for example form a spherical or generally spherical segment of less than half a sphere.

In a further embodiment the outer cross-section corresponds to an overall outer cross-section of the transfer pad. Therefore the stamping surface may have a generally cylindrical outer cross-section or outline corresponding in size and shape to the outline of the cylindrical section.

In one embodiment the dental coloring stamp further comprises a housing having a body and a cover. The transfer pad may be fixed in the body. Further the cover and the body are preferably shaped and sized for sealingly mating with one another such that a seal is established. The body preferably forms or comprises a reservoir for holding the dental coloring solution. The reservoir preferably has an opening which is closed by the transfer pad. The opening preferably is formed by a passageway through the body. The transfer surface may face in a direction from the reservoir toward outside of the opening. For example the transfer pad may be received in the opening and protrude over the boundary of the body. Further the cover is preferably removably placeable on the body to as to seal the reservoir.

In one embodiment the body forms a well which has a bottom wall from which a circumferential side wall protrudes. The transfer pad may be fixed at a surface opposite of the transfer surface at the bottom wall of the well. A circumferential space is preferably provided between the transfer pad and the side wall.

In a further embodiment the dental coloring stamp comprises a first transfer pad soaked with a first coloring solution for providing an enamel color shade, and a second transfer pad soaked with a second coloring solution for providing a dentin color shade. The first and the second transfer pad preferably have a first and a second stamping surface, respectively. The dental coloring stamp of this embodiment preferably has a housing comprising a first well and a second well which are movable relative to each other. The first and second well may be connected by a hinge and thus movably arranged relative to each other. In this embodiment the first transfer pad is arranged in the first well and the second transfer pad is arranged in the second well. This embodiment enables stamping of the dental restoration precursor from opposite sides. In particular the embodiment enables stamping of the dental restoration precursor from opposite sides generally simultaneously with only one dental coloring stamp.

In a further embodiment the dental coloring stamp comprises a dental coloring solution. The dental coloring solution may comprises a solution comprising a solvent and a coloring agent comprising metal ions selected from one or more of Fe, Cr, Ni, Tb, Er, Pr, Mn. Further the dental coloring solution may comprise a fluorescing agent comprising ions of Bi.

A "fluorescing agent" shall mean an agent showing fluorescence in the region of visible light (about 380 to about 780 nm).

The solution may contain only one of the following coloring ions: ions of Er, Pr, Mn or Tb or a combination thereof: Er and Pr; Er and Mn; Er and Tb; Pr and Mn; Pr and Tb; Mn and Tb; Er, Pr and Mn; Er, Pr and Tb; Er, Mn and Tb; Pr, Mn and Tb, Er, Pr, Mn and Tb. The solvent may be selected from water, alcohols, ketons, glycols and combinations thereof.

In a further aspect the invention relates to a kit of parts, comprising a dental coloring stamp of the invention and at least one container containing a dental coloring solution. The kit of parts may comprise a plurality of containers containing different dental coloring solutions providing different colors. The coloring solutions may be composed so as to provide a sintered dental restoration with a color selected from a standardized color scheme. One standard color scheme is known as VITA classical A1-D4 Shade Standard from the company VITA Zahnfabrik, Germany. Further the kit may comprise instructions for use with instructions associated with the method steps of the invention.

In a further aspect the invention relates to a method of coloring a dental restoration. The method comprises the steps of:

providing a precursor of a dental restoration, the dental restoration precursor having two opposite sides in each of three dimensions of a Cartesian coordinate system;

providing a dental coloring stamp soaked with a dental coloring solution; and stamping at least 80%, more particularly at least 90%, of the surface of one side of the dental restoration precursor and the dental coloring stamp at least one time onto each other; and firing the dental restoration precursor to form the dental restoration.

The dental coloring solution comprises a solution comprising a solvent, a coloring agent comprising metal ions selected from one or more of Fe, Cr, Ni, Tb, Er, Pr, Mn, and a fluorescing agent comprising ions of Bi.

In one embodiment the method further comprises the step of removing the dental restoration precursor and the dental coloring stamp from each other within a determined timeperiod of 3 seconds after stamping.

In a further embodiment the method further comprises the step of immersing the dental restoration precursor directly in a bath of a second dental coloring solution prior to stamping. Thus, the dental restoration precursor may be essentially uniformly colored with a base color. The stamping step according to the method of the invention thus provides dental restoration precursor with an additional color gradation. In a further embodiment the dental restoration precursor is a precursor of a dental crown or bridge. In a preferred embodiment the stamped side corresponds to a precursor of the occlusal or incisal side of the dental restoration.

In a further embodiment the method further comprises the step of stamping the same side of the dental restoration precursor at least a second time. The same side may be stamped three or four times or more often. Thus, the intensity of the coloring of the dental restoration may be adjusted as desired.

In an embodiment the method further comprises the step of performing the stamping based on observing a penetration depth of the dental restoration precursor to a pre-determined position at the dental restoration precursor. The pre-determined position may correspond to a level between the occlusal or incisal surface of the dental restoration precursor and an opposite surface of the same dental restoration precursor.

In a further embodiment the method further comprises the step of marking the pre-determined position at the dental restoration precursor prior to stamping. The marking may be performed by drawing a line onto the outer surface of the dental restoration precursor. This line is indicative of the level between the occlusal or incisal surface of the dental restoration precursor and the opposite surface of the same dental restoration precursor. Further this line is preferably approximately parallel to the occlusal or incisal surface of the dental restoration precursor. The step of drawing the line may be performed by use of a pencil, for example. Further the method may comprise the step of erasing the marked pre-determined position from the dental restoration precursor.

DETAILED DESCRIPTION OF THE INVENTION

FIGS. 1A-1D illustrate the technical principle on which the invention is based. A dental restoration precursor 100 is provided made of a pre-sintered ceramic or glass-ceramic material. Further a dental coloring stamp 10 is provided. The coloring stamp 10 has a transfer pad 11. The transfer pad 11 is formed of an open-celled elastic sponge. Thus, the transfer pad is configured to dischargeably absorb a liquid. In the example the transfer pad 11 is soaked with the dental coloring solution. Further, the transfer pad 11 has a minimum thickness in a stamping dimension X so that it can conform to the shape of the dental restoration precursor 100, in the example to the occlusal or incisal surface of the dental restoration pre-cursor 100. The thickness of the transfer pad 11 is preferably further configured to provide a desired capacity for the coloring solution absorbable within the transfer pad 11. The transfer pad 11 further has an obtuse free transfer surface 12 which extends in dimensions essentially laterally to the stamping dimension X. The transfer surface 12 forms the portion of the transfer pad 11 which is intended for being brought into contact with the dental restoration precursor 100.

Figure 1A:
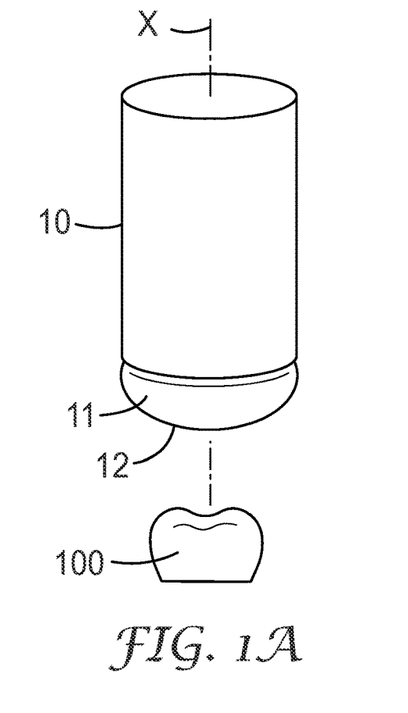
FIGS. 1A-1D are perspective views of a dental coloring stamp according to an embodiment of the invention.
Figure 1B:
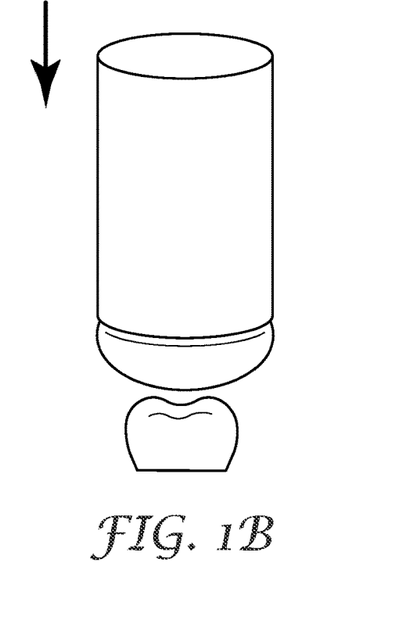
Figure 1C:
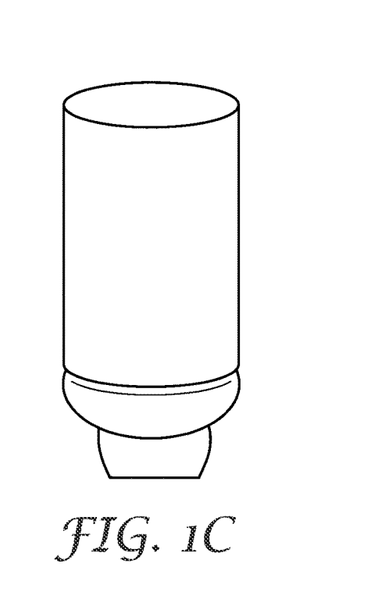
Figure 1D:
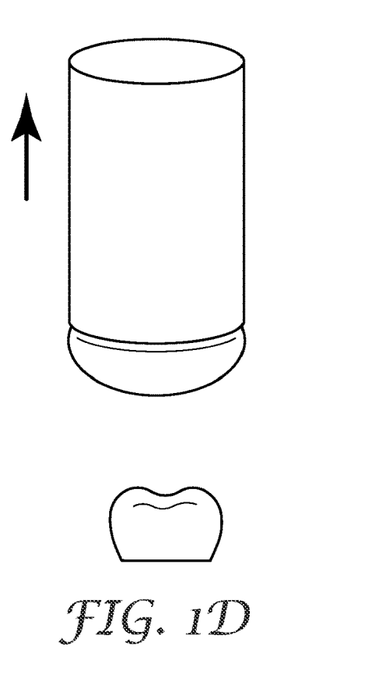

As illustrated in FIG. 1B the coloring is performed by stamping one side of the dental restoration precursor 100 and the dental coloring stamp 10 onto each other. Thereby the transfer pad 11 is compressed and coloring solution is discharged therefrom. The discharged coloring solution is soaked into the dental restoration precursor 100. This is due to the fact that the dental restoration precursor is made of open-celled or porous material. Due to capillary effects the coloring solution automatically permeates into the open-celled material the dental restoration precursor 100 is made of. The travel of the coloring solution into the material automatically stops dependent on the amount of coloring solution soaked into the material, and the amount of coloring solution soaked in the material can be controlled by the frequency and time period for which the dental restoration precursor 100 and the transfer pad 11 are stamped onto one another. In this way the dental restoration precursor 100 can be partially soaked with coloring solution in a controlled and reproducible manner. That partial coloring of the dental restoration precursor results in the dental restoration to exhibit a color gradient after sintering. It is noted that although it is referred to a color or color gradient of the dental restoration precursor, any color or color gradation may only become visible in its final optical appearance after sintering the dental restoration precursor.

Accordingly a dental restoration may be provided with a color gradation by stamping a essentially the full side of the dental restoration precursor, meaning by stamping more than 80% of the surface of that side at once. Therefore the transfer pad 11 in dimensions laterally to the stamping dimension X is greater than the side of the dental restoration precursor to be stamped. In particular the transfer pad 11 in dimensions laterally to the stamping dimension X is preferably greater than an area at the greatest cross-section of a human molar tooth in a plane parallel to the occlusal plane of that tooth. Further each lateral dimension of the transfer pad 11 may be selected about 1.2 to 1.5 greater than the corresponding dimension at the greatest cross-section of the human molar tooth. This is to account for the shrinkage factor between the dental restoration precursor and the finished dental restoration. Based on these considerations it has been found that the transfer pad 11 desirably has lateral dimensions that are greater than a circular area of 10 mm in diameter.

The intensity and/or structure of the color gradation may be controlled by the time of stamping the dental restoration precursor 100 and the number of repetitions of the stamping step. In particular, the time-period between the first contact of the coloring stamp 10 dental restoration precursor 100 (FIG. 1B) and the removal of the coloring stamp 10 from the dental restoration precursor 100 (FIG. 1C) typically impacts the amount of coloring solution being transferred from the transfer pad 11 to the dental restoration precursor 100. Such time-period is also referred to as "stamping time-period" herein. Further, the intensity and/or structure of the color gradation may be controlled by the penetration depth of the dental restoration precursor 100 into the transfer pad 11. In particular the dental restoration precursor 100 may be stamped multiple times at different penetration depths.

Figure 2A:
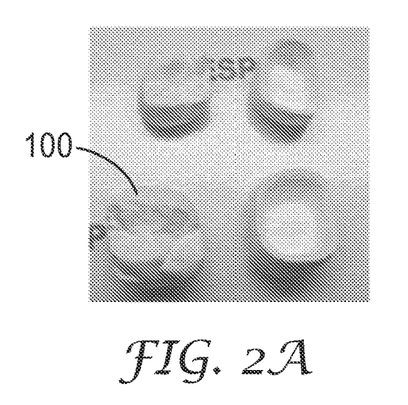
FIGS. 2A-2F illustrate an embodiment of the method of the invention.
Figure 2B:
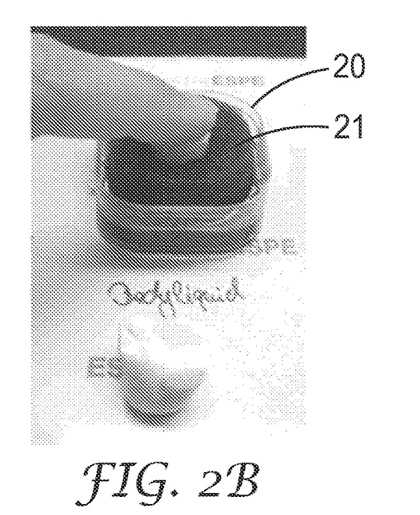

FIGS. 2A-2F illustrate the method of the invention in more detail. In one step as shown in FIG. 2A a precursor 100 of a dental restoration is provided. In the example a precursor of a dental crown is shown in a top view (on the left) onto the topside (or occlusal/incisal side) and a bottom view (on the right) onto the underside (or the substructure-facing side). A suitable substructure onto which the finished crown may be fixed may be a natural tooth stump, a dental abutment or dental implant. The crown in the example is made of a ceramic material, in particular of a pre-sintered open-celled zirconia material.

The dental restoration precursor 100 is stamped with the underside onto the dental coloring stamp 20 (shown in FIG. 2B) and removed from the dental coloring stamp 20 again. Although the underside of the dental crown forms a cavity the elastically deformable stamping pad 21 is configured to penetrate into the cavity so as to transfer coloring solution to the underside. The stamping step is repeated four times at a stamping time-period of 3 seconds per stamping. Thereby the stamping is repeated on the same side of the dental restoration precursor. In this step the dental restoration precursor is provided with a dentin color shade. Such dentin color shade is intended to resemble the dentin color shade of a natural tooth.

The combination of stamping the enamel color shade at one side of the precursor followed by stamping the dentin color shade at the opposite side of the dental restoration precursor (or vice versa) has been identified as an efficient way to mimic a transition (referred to as "dentin-enamel transition" herein) of the dentin/enamel colors similar to a natural tooth.

An advantage of the stamping procedure of the invention results from the fact that the penetration depth of the dental restoration precursor into the (elastically deformable) transfer pad can be easily controlled. For example a user may press the dental restoration precursor into the transfer pad to a desired depth by adapting finger pressure and visually observing the penetration depth. This procedure can be facilitated by a thin line drawn (for example with a pencil) on the restoration precursor prior to stamping. Thus the penetration depth of the dental restoration precursor into the transfer pad can be pre-determined to control the position of the dentin-enamel-transition.

Figure 2C:
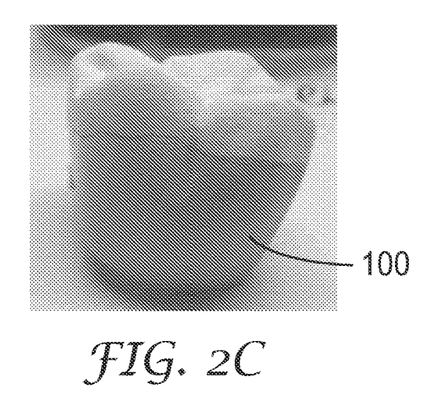
Figure 2D:
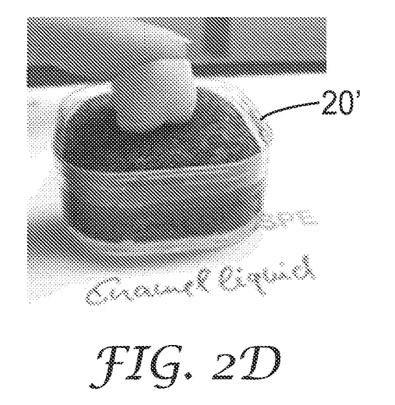
Figure 2E:
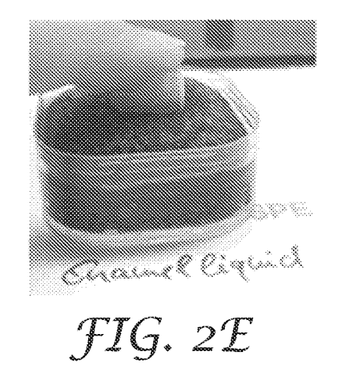

FIG. 2C shows the dental restoration after stamping in a drying step. In this step the solvent of the coloring solution is substantially eliminated.

The dental restoration precursor 100 in a further step is stamped with the topside onto a dental coloring stamp 20' (shown in FIG. 2D) and removed from the dental coloring stamp 20' again. The stamping step is repeated two times at a stamping time-period of 3 seconds per stamping. In this step the dental restoration precursor is provided with an enamel color shade. Such enamel color shade is intended to resemble the enamel color shade of a natural tooth.

Figure 2F:
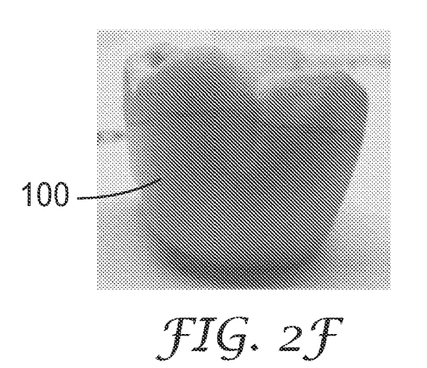

FIG. 2F shows the dental restoration precursor 100 in a drying step for removing the solvent of the coloring solution from the dental restoration precursor 100.

The order of the stamping steps using dentin and enamel color may be reversed relative to the previous description or repeated alternately, as appropriate.

In the example of FIGS. 2A-2F the dental coloring stamp 20/20' is configured for standing, for example on table top and the dental restoration precursor 100 is moved relative to the dental coloring stamp 20/20'.

In a further example as illustrated in FIGS. 3A-3F a dental coloring stamp 30 is provided which is configured as a hand-held device. The dental coloring stamp in this example is moved and the dental restoration precursor 100 is supported on a table top.

Figure 3A:
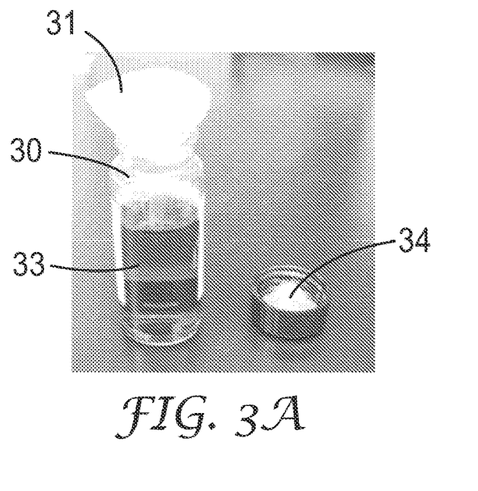
FIGS. 3A-3F illustrate a further embodiment of the method of the invention.

In FIG. 3A the dental coloring stamp 30 is prepared for use. The dental coloring stamp 30 has a reservoir 33 holding a sufficient amount of coloring solution for coloring multiple dental restoration precursors. The dental coloring stamp 30 further has a transfer pad 31 which is uncovered by removing a cap 34 of the dental coloring stamp 30.

Figure 3B:
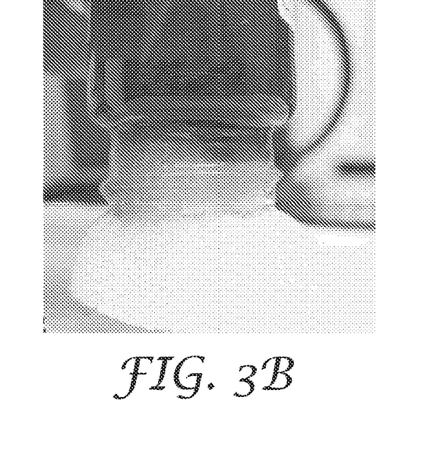

In FIG. 3B the dental coloring stamp 30 is pushed with the transfer pad 31 onto a surface so as to cause the transfer pad 31 to soak with coloring solution.

Figure 3C:
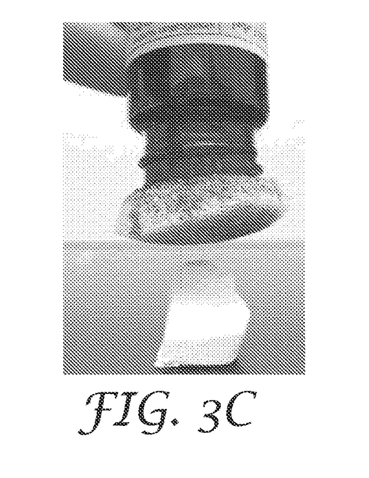
Figure 3D:
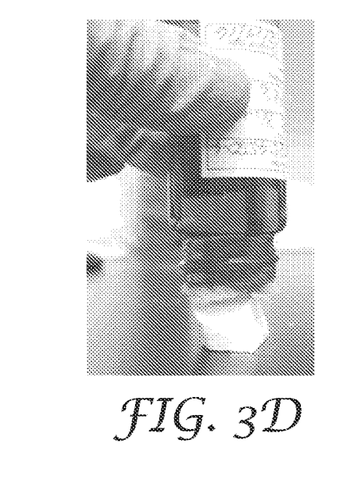
Figure 3E:
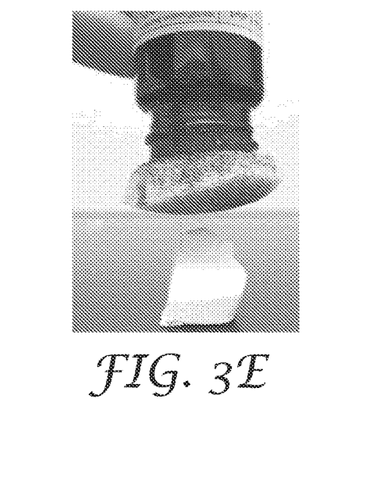

The dental coloring stamp 30 is then used to stamp a side of a dental restoration precursor 100 for a stamping time-period of 3 seconds and removed from the dental restoration precursor 100 as illustrated in FIGS. 3C through 3E.

Figure 3F:
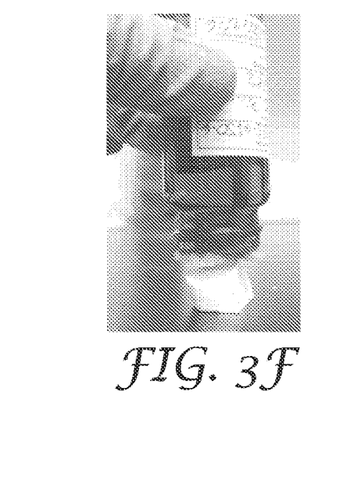

FIG. 3F illustrates in cross-sections through the dental restoration precursor 30 that the coloring solution has penetrated into a portion 101 of the dental restoration 100.

Figure 4A:
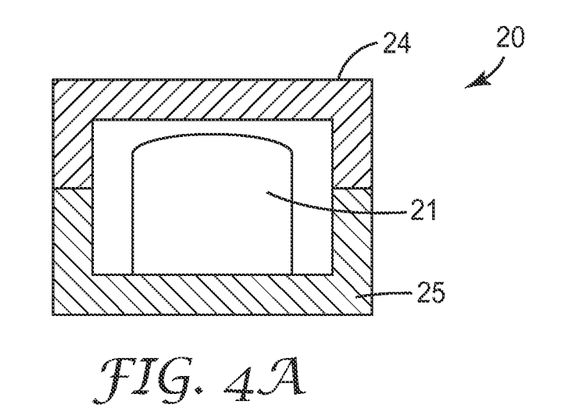
FIGS. 4A, 4B are cross-sectional views of a dental coloring stamp according to an embodiment of the invention.
Figure 4B:
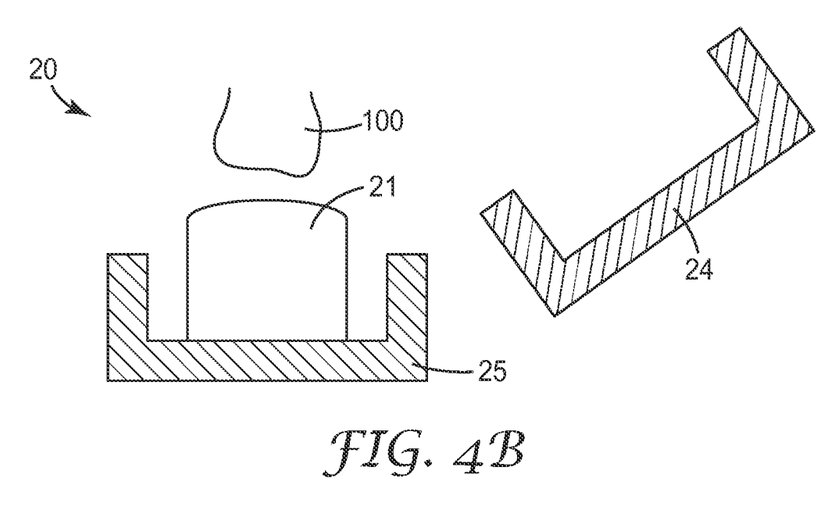

FIGS. 4A, 4B show a dental coloring stamp 20 in more detail. The dental coloring stamp 20 has a bottom well 25 and a cover 24. A transfer pad 21 is attached, for example glued, to the bottom well 25. In the example the dental coloring stamp 20 is configured for single use with the transfer pad 21 being pre-soaked with a coloring solution of a certain color selected from a plurality of different colors. However, in another example the transfer pad 21 of the dental coloring stamp 20 may not contain any coloring solution. In such an example the coloring solution may be added just prior to use. The cover 24 is used to protect the transfer pad 21 from the environment, for example during transport of the device from the factory in which the dental coloring stamp 20 is manufactured to the user (for example in a dental lab). Further a dental coloring stamp 20 which is intended for multiple uses the cover 24 can be used to seal the transfer pad 21 soaked with coloring liquid until any next use.

FIG. 4B shows the dental coloring stamp 20 supported on a table top with the cover 24 removed from the bottom well 25, and a dental restoration precursor 100 positioned relative to the transfer pad 21.

Figures 5A, 5B:
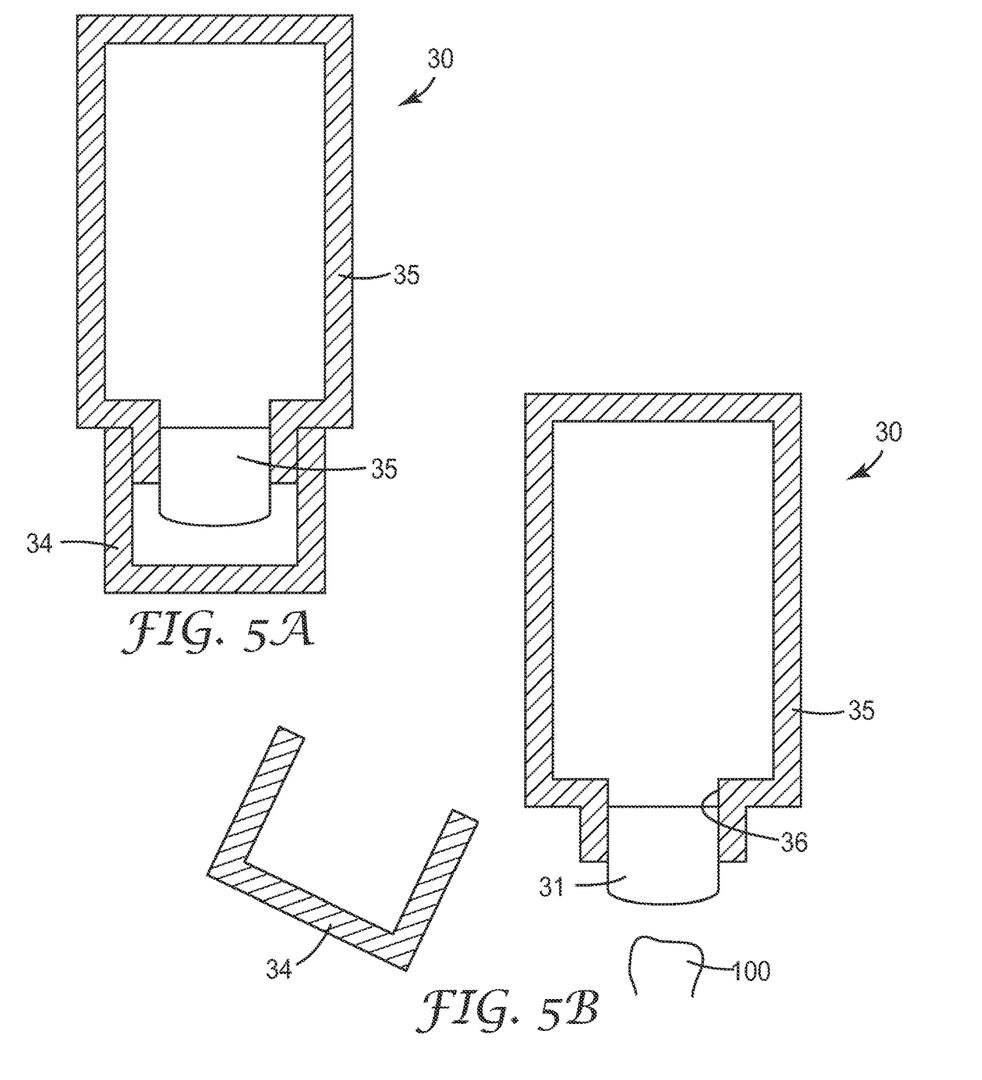
FIGS. 5A, 5B are cross-sectional views of a dental coloring stamp according to a further embodiment of the invention.

FIGS. 5A, 5B show an alternative dental coloring stamp 30 in more detail. The dental coloring stamp 30 has a body 35 and a cover 36 which in combination form a housing. Further the body 35 forms a reservoir for the coloring solution. A transfer pad 31 is received in an opening 36 of the reservoir. In the example the dental coloring stamp 30 is configured for multiple use. Accordingly a sufficient quantity of coloring solution for coloring a plurality of dental restoration precursors is provided in the reservoir.

FIG. 5B shows the dental coloring stamp 30 in use with the cover 34 removed from the body 35. A dental restoration precursor 100 is positioned relative to the transfer pad 31.

Example

A sponge (open celled with average cell size of 505±158 μm) was mounted in a 35 mm×35 mm Polystyrene container and saturated with Lava Plus™ Enamel Liquid (Lot #548286, expiration date 2017-03). A second container was prepared by mounting a stub made from composite (Pattern Resin from GC Company) into the bottom of the container. The stub size was selected to be slightly smaller than the inside of an average size molar crown. A second sponge from the same sponge material was prepared by cutting a cavity into one side to allow fit over the stub mounted in the bottom of the container. The sponge was mounted in the container such that the stub was completely covered. The sponge was then saturated with Lava Plus™ Body Shade Liquid A2 (lot #504874, expiration date 2016-01).

A molar crown was milled from Lava Plus™ High Translucency Zirconia. The crown was removed from the mill blank by cutting the sprues with a dental handpiece. The residual sprue stumps on the crown surface were removed with a dental handpiece and smoothed with sandpaper. The milling dust was removed with a soft bristled brush and cleaned by gently blowing with an air nozzle.

The transition between enamel and body region was marked by drawing a slight pencil mark in the location where the enamel shade should border the body shade. The crown was then gently pressed into the sponge containing the Lava Plus™ Body Shade Liquid A2 up to the pencil mark and immediately released. This pressing process was repeated 4 times. Care was taken to ensure that the stub mounted beneath the sponge was centered inside the crown. After briefly letting the crown sit to soak up shading liquid from its surface, the crown was turned over, and gently pressed 2 times into the sponge containing the Lava Plus™ Enamel Liquid EL.

The crown was then placed into the Lava Therm™ and fired in the classical Lava Plus firing program and thus converted from its pre-sintered to its finally sintered stage.

The resulting molar crown displayed a natural gradient as expected for a natural-gradient-shading crown by painting shading liquid onto the crowns with a brush. The shading process was at least twice as fast as the natural-gradient-shading method.

In one trial which was conducted in accordance with the Example the time period required for providing a dental restoration precursor with a coloring solution for appropriately coloring a dental restoration finished from this dental restoration precursor was about 50 seconds as opposed to about 3 Minutes in a comparative trial in which a dental restoration precursor was provided with coloring solution by use of a brush.

The invention claimed is:

1. A dental coloring stamp, comprising a dental coloring solution and a transfer pad for transferring the dental coloring solution to a precursor of a dental restoration, the transfer pad being at least partially formed of an open-celled elastic sponge, the transfer pad having a thickness along a stamping dimension and a transfer surface which extends in dimensions essentially laterally to the stamping dimension, wherein the transfer pad in dimensions laterally to the stamping dimension is greater than a circular area of 10 mm in diameter, and wherein the dental coloring solution comprises a solution comprising a solvent, a coloring agent comprising metal ions selected from one or more of Fe, Cr, Ni, Tb, Er, Pr, Mn, and a fluorescing agent comprising ions of Bi.

2. The dental coloring stamp of claim 1, wherein the transfer pad includes a stamping surface, and wherein the stamping surface has a convex dome-shape being defined by an outer cross-section with a minimum width in a plane laterally to the stamping dimension, a height along the stamping dimension between said plane and the dome apex, and a ratio between the height and the minimum width of less than 1:1, respectively.

3. The dental coloring stamp of claim 1, further comprising a housing having a body in which the transfer pad is fixed and a cover, wherein the cover and the body are shaped and sized for sealingly mating with one another.

4. The dental coloring stamp of claim 3, wherein the body comprises a reservoir for holding the dental coloring solution, the reservoir having an opening being closed by the transfer pad, wherein the transfer surface faces in a direction from the reservoir toward outside the opening.

5. The dental coloring stamp of claim 3, wherein the body forms a well having a bottom wall from which a circumferential side wall protrudes, the transfer pad at a surface opposite of the transfer surface being fixed at the bottom wall of the well.

* * * * *